US012582348B2

(12) United States Patent (10) Patent No.: US 12,582,348 B2

Marcu et al. (45) Date of Patent: Mar. 24, 2026

(54) DEVICE AND METHOD FOR INSPECTING A HAIR SAMPLE

(71) Applicant: L'OREAL, Paris (FR)

(72) Inventors: Tal Marcu, Clichy (FR); Thierry Wasserman, Clichy (FR)

(73) Assignee: L'Oreal, Paris (FR)

( * ) Notice: Subject to any disclaimer, the term of this patent is extended or adjusted under 35 U.S.C. 154(b) by 1108 days.

(21) Appl. No.: 17/433,084

(22) PCT Filed: Jan. 23, 2020

(86) PCT No.: PCT/EP2020/051681

§ 371 (c)(1),
(2) Date: Aug. 23, 2021

(87) PCT Pub. No.: WO2020/173628

PCT Pub. Date: Sep. 3, 2020

(65) Prior Publication Data

US 2022/0087596 A1 Mar. 24, 2022

(30) Foreign Application Priority Data

Feb. 27, 2019 (EP) ..................................... 19159804

(51) Int. Cl.
*A61B 5/00* (2006.01)
*A45D 44/00* (2006.01)
(Continued)

(52) U.S. Cl.
CPC ............ *A61B 5/448* (2013.01); *A61B 5/0077* (2013.01); *G01J 3/021* (2013.01); *G01J 3/0272* (2013.01);
(Continued)

(58) Field of Classification Search
CPC .................. A61B 5/448; A61B 5/0075; G06T 2207/30088; G06T 7/0012; G06T 7/10;
(Continued)

(56) References Cited

U.S. PATENT DOCUMENTS 5,478,238 A 12/1995 Gourtou et al.
6,907,138 B1 6/2005 Hoffman et al.
(Continued)

FOREIGN PATENT DOCUMENTS

CN 108592796 A * 9/2018 ............. G01B 11/00
EP 0443741 A1 8/1991
(Continued)

OTHER PUBLICATIONS

International Search Report issued on Apr. 15, 2020 in PCT/EP2020/051681 filed on Jan. 23, 2020.
(Continued)

*Primary Examiner* — Ross Varndell
(74) *Attorney, Agent, or Firm* — Christensen O'Connor Johnson Kindness PLLC

(57) ABSTRACT

The present application is directed to a device for inspecting a keratinous surface of a user, preferably a hair sample, comprising a housing in which an image sensor is arranged to receive measurement light emitted from a measuring area configured to accommodate the keratinous surface, through a measurement window in a front wall of the housing, over a corresponding imaging light path, the device being further equipped with an illumination ring arranged in the housing rear of the measurement window around the imaging light path, said illumination ring having two opposed partially peripheral illumination portions separated by two opposed complementary partially peripheral non-illuminating portions, the illuminating portions being further configured to illuminate the measuring area through the measurement
(Continued)

Figure 1:
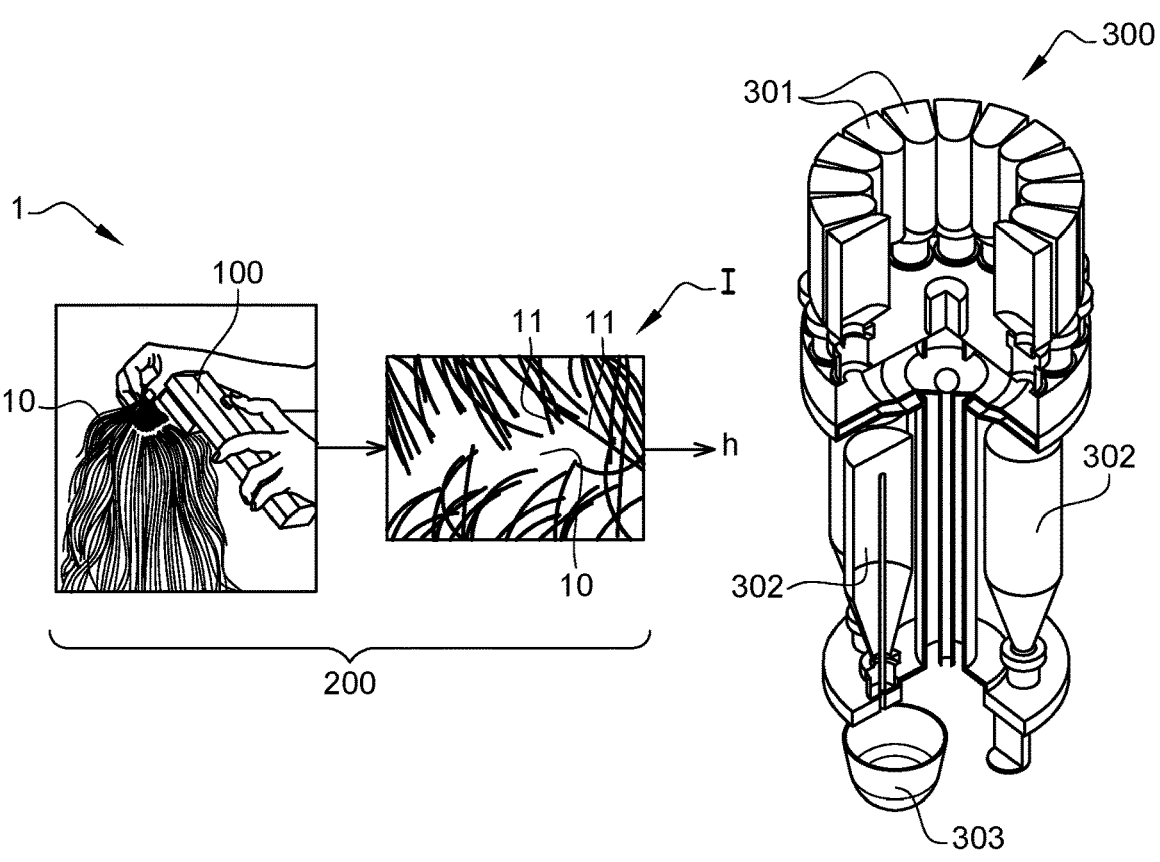

window over a illumination light path, said illumination light path having an angle of incidence comprised between 30 to 60°, preferably about 45°.

20 Claims, 3 Drawing Sheets

(51) Int. Cl.
| | | |
|---|---|---|
| *G01J 3/02* | (2006.01) | |
| *G01J 3/10* | (2006.01) | |
| *G01J 3/50* | (2006.01) | |

(52) U.S. Cl.
CPC .......... *G01J 3/10* (2013.01); *A45D 2044/007* (2013.01); *A61B 2560/0431* (2013.01); *A61B 2562/0233* (2013.01); *G01J 2003/102* (2013.01); *G01J 3/501* (2013.01); *G06T 2207/30088* (2013.01)

(58) Field of Classification Search
CPC ............. G06T 7/90; G06T 2207/10048; G06T 2207/20081; G06T 2207/20084; G06T 2207/30201; G06N 20/00
See application file for complete search history.

(56) References Cited

U.S. PATENT DOCUMENTS

| | | | |
|---|---|---|---|
| 9,316,580 | B2 | 4/2016 | Landa et al. |
| 9,519,927 | B1 | 12/2016 | Tuan et al. |
| 2008/0068604 | A1 | 3/2008 | Grossinger et al. |
| 2009/0036800 | A1 | 2/2009 | Rabin et al. |
| 2010/0328667 | A1 | 12/2010 | Wegmuller et al. |
| 2012/0253203 | A1 | 10/2012 | Weston et al. |
| 2014/0216492 | A1 | 8/2014 | Magri Amaral et al. |
| 2014/0276103 | A1* | 9/2014 | Lee .................... A61B 10/0041 600/476 |
| 2015/0089751 | A1* | 4/2015 | Landa .................... B65D 83/04 8/405 |
| 2016/0339274 | A1* | 11/2016 | Landa .................... G01N 21/27 |
| 2018/0168456 | A1 | 6/2018 | Lim et al. |
| 2018/0247365 | A1* | 8/2018 | Cook .................... G02B 21/367 |
| 2021/0082117 | A1* | 3/2021 | Erdogan ............... A61B 5/448 |
| 2024/0041390 | A1* | 2/2024 | Rattner .................. A61B 5/744 |

FOREIGN PATENT DOCUMENTS

| | | | | |
|---|---|---|---|---|
| KR | 101456942 | B1 | 11/2014 | |
| WO | 2004002300 | A2 | 1/2004 | |
| WO | 2011024160 | A1 | 3/2011 | |
| WO | WO-2017207455 | A1 * | 12/2017 | ............. A61B 5/445 |

OTHER PUBLICATIONS

European Search Report mailed Aug. 13, 2019, issued in European Application No. 19159804.4, filed Feb. 27, 2019, 3 pages.

\* cited by examiner

DEVICE AND METHOD FOR INSPECTING A HAIR SAMPLE

The present invention relates to a device and method for inspecting a hair sample and/or a surface of the scalp of a person comprising hairs.

The device and method are particularly directed to the analysis and treatment of human hairs, and more particularly, is to be used in conjunction with a method and system for bleaching or dyeing hairs such as disclosed in document EP0443741.

The health and beauty industry leverages advances in technology to improve the consumer experience with their products and services. There is a deep trend to offer products that are tailored to the user's needs and fit its specific traits. This trend is generally called "personalization".

"Personalization" can pertain to any body part but is of particular interest for exposed body parts such as the face (makeup or care products, in particular foundation) and scalp/hairs (care or dyeing products for example).

It is known to offer and recommend foundation makeup products based on at least one property of the user's skin (such as "Le Teint Particulier"® by LANCÔME®). It is also known to offer and recommend hair products based on some properties of the hairs (see for example EP0443741 previously mentioned, and documents WO2004002300A2 and U.S. Pat. No. 9,316,580B2).

"Personalization" goes beyond the mere offering of a more or less broad range of products corresponding each to a dedicated category of users, the challenge often being to be able to recommend the most appropriate product to the concerned user depending on its personal traits.

As detailed in the previously cited documents, "personalization" generally comprises a first analysis step aiming at obtaining data that are specific to said user, the data being then used to determine an appropriate subsequent treatment and/or product(s) to be applied to the user concerned body part.

Until recently, the analysis step was often used to be performed manually or visually by an expert such as a hairdresser or a beauty adviser. It is for example known to address the user with a specific questionnaire, the answers of which are used to determine the allegedly most suitable product (e.g US20140216492). Of course such a method is highly variable and lacks precision.

In order to improve the relevancy and reliability of the product recommendation, some or all the steps may be performed using tools and devices and even be automated.

For example, obtaining data from the user's concerned body part can be done through measurement using an appropriate measurement device (called a "reader") for obtaining one or more specific features that are looked after for determining the appropriate treatment or product. An example of such a device is the CAPSURE reader marketed by X-RITE and able to return a color data code of the skin of a user (see for example document US20100328667 although it is not explicitly directed to skin or keratinous surfaces).

The collected data may then be fed (possibly with other additional data) to a computing unit that will help determining the most suitable product according to a at least one set of rules (rules of applications).

The subsequent treatment or product determined according to the collected data may be a ready-made product chosen from a catalogue or in a database (such as in documents U.S. Pat. No. 5,478,238 or U.S. Pat. No. 9,519,927 disclosing methods for finding a matching foundation products) or a personalized product, the composition of which has been determined based on the previously obtained data.

The recommended product may then be bought or ordered by the user. In case of a personalized product (or custom-made product), said personalized product may be then manufactured on site, directly at the point of sale, in the shop or in the beauty/hair salon by a device able to mix components according to the personalized composition and dispense said composition. The personalized product may also be ordered by the user for a later delivery.

As a full example of such a system, the above mentioned document U.S. Pat. No. 9,316,580B2 discloses a method of performing a customized treatment of keratinous fibers comprising a diagnostic step using an optical reader configured to acquire a spectrum of the hairs, said spectrum being used to compute a subsequent hair treatment composition, the appropriate composition being then made and dispensed by a corresponding device. One may also refer to document WO2011024160A1.

As mentioned above, obtaining reliable, objective and relevant data from the user may be particularly challenging. This is especially the case for hairs or scalp due to their specific texture and environment.

Depending on the desired information that are looked for, different techniques may be used.

Document KR-A1-101456942 discloses a hair and scalp condition diagnostic device comprising a sensor unit to diagnose a user's hair or scalp condition objectively by comparing previously stored hair or scalp samples based on diagnosis signals diagnosed by a hair or scalp condition. In particular, the device may comprise an image sensor for acquiring images of an area of the scalp. The acquired images may then be processed through an image analysis module using for example light intensity recognition, color recognition or contrast analysis in order to determine some properties of the hairs such as number of hairs, diameter, etc.

Document WO2017207455 filed in the name of the present applicant also proposes a method for analyzing a condition of the scalp and/or hairs comprising the step of taking pictures under different lighting conditions (white light and UV-Blue light), in order to improve detection of the hairs and better reveal light and white hairs. The images are then processed namely through contrast analysis in a complementary way.

Document US2012253203 discloses a method for imaging a skin surface presenting hairs, such as an area of the scalp in order to determine a skin and hair growth condition. The method comprising taking pictures of the concerned surface under different viewing angles, said pictures being then potentially processed by computer analysis in order to determine properties such as number of hairs protruding from the skin surface, thickness of hairs, diameter or cross sectional shape of hairs, length of hairs protruding from the surface.

Document US2009036800 pertains to a hair densitometer. The densitometer works by taking magnified pictures of an area of the scalp. Hairs visible in the image may be counted and measured by a technician or by any suitable automated system.

For such image based analysis methods using a device able to acquire an image of the desired keratinous surface, the quality of the acquired image is paramount and there is a general need to ensure the required quality of said image. This is particularly true for methods in which the acquired image is further processed through image analysis algorithms, in particular through image recognition algorithms or machine learning algorithms. Indeed, the results of such algorithms highly depend on the quality of the input image data.

This is also particularly true in the specific area of hair dyeing or bleaching, where a reliable and true diagnostic of the initial hair parameters (such as hair color) is paramount since it will have a strong impact on the final color to be obtained.

The present invention aims at providing an improved device for inspecting a scalp surface of a user comprising hair and/or a hair sample.

To this end, the present application pertains to a device comprising a housing in which an image sensor is arranged to receive measurement light emitted from a measuring area configured to accommodate the keratinous surface, through a measurement window in a front wall of the housing, over a corresponding imaging light path.

According to the present application, the device is further equipped with an illumination ring arranged in the housing rear of the measurement window around the imaging light path, said illumination ring having two opposed partially peripheral illumination portions separated by two opposed complementary partially peripheral non-illuminating portions, the illuminating portions being further configured to illuminate the measuring area through the measurement window over a illumination light path, said illumination light path having an angle of incidence on the measurement area comprised between 30 to 60°, preferably about 45°. According to the present application, the device is configured so that both illumination portions may be switched on when an image is taken.

Simply said, Illumination is implemented using a "ring-light" with only two quarters facing each other in use in a 45:0 measurement configuration. It has been indeed found that by associating an image sensor for acquiring an image of the keratinous surface arranged in the measuring area, to a partial illumination ring alternating non-illuminating portions and illuminating portions (called "two quarters" illumination), it improved the overall image quality by preventing some undesired reflections.

Advantageously, the illuminating portions of the light ring extend over a sector of 30 to 60°, preferably over a sector of 45°.

Also, by using a 45:0 measurement, lighting collection is greatly improved. 0:45, 45:0 and sphere measurement are usually considered for spectrophotometers but appears to be also important with an image sensor. Indeed, it appears that the main color information from the hairs is perceived in this configuration.

In the specific case of hairs, the hairs can be modelled by a cylindrical object and when illuminating along the hair axis, the specular light is reflected in a conical fashion. When illuminating at 45 degrees, this reflected cone has a 45 degree angle and does not enter the measurement window, and thus does not follow the imaging light path. Advantageously, the two dark quarters would be roughly perpendicular to the hair follicles and scatter light into the measurement window along the imaging light path if they were in use.

An arrangement according to the present application allows for the acquisition of images with a low specular reflection. An alternative standard method for doing this would be using cross polarization between the illumination and the lens. However, due to the birefringent nature of hair, it cannot be done.

In addition, having two-quarter illumination configuration blurs the shadows of the hair on the scalp compared to illumination from one or two 45 degree directions. The distinct shadows could otherwise be confused with hair follicles.

The two-quarter illumination configuration is also less sensitive to positioning relative to the hair. When measuring hair on scalp, the follicles have a general direction, but are not perfectly aligned.

Although such an arrangement may be common with spectrophotometer, it is not known to be used with image sensor for image analysis.

Preferably, the measurement area is substantially located at the measurement window, and in particular within a distance of less than 2 mm of said measurement window, preferably about 1 mm.

Advantageously, the imaging light path is equipped with a telecentric lens, preferably a double telecentric lens.

A telecentric lens allows for an image acquisition from a single direction angle, similarly to the way a spectrophotometer collects light. This also allows to use the 45/0 degree illumination configuration using an imaging device.

In addition, the use of a telecentric lens results in less vignetting than a regular lens and in more uniformity in acquisition of light over the whole image. A regular lens has a $\theta^4$ intensity dependence, while a telecentric one, $\theta^2$. Colour alteration is also reduced.

Telecentric lens also gives fringe benefit and lowers distortion over the image. This allows for uniform geometrical measurements over the whole image, such as hair diameter, density, etc.

The telecentric lens may be telecentric on the image side or the object side (preferred), better be telecentric on both sides, i.e. double telecentric.

Double telecentric lens allows for an easier implementation of an hybrid design having both a regular RGB sensor and a multispectral component. Passing through a cube beamsplitter with a non telecentric design would result in image aberrations that can more easily be corrected with a telecentric design.

One will also note that in case of using dichroic bandpass filters, those are very sensitive to input angle. A telecentric design allows for an equal input angle over the whole filter particularly advantageous in the multispectral implementation using a multispectral image sensor.

Preferably, the imaging light path is equipped with a 0.5× magnification lens.

Such a magnification value is a good compromise between field-of-View, resolution, and depth of field. In the specific hair analysis application, hair diameter is on the order of 70 microns, and between 5 to 10 pixels across each hair is usually need in order to correctly process the image though an image analysis module. With a pixel pitch on the order of 5 microns, we are getting an object side resolution of 10 microns.

Preferably, the imaging light path is fixed focus.

Preferably again the depth of field is between 0.5 mm and 1 mm.

Advantageously, the imaging light path has a telecentricity below 1 degree.

An aperture between f/8 and f/16 of the optical system (lens) may be advantageously used resulting in a resolution of around the pixel size and importantly a depth of field of +/−5 mm to 10 mm. When the system is fixed focus without an auto-focus mechanism, the large depth of field allows to capture images in focus over the whole hair and scalp range.

The illuminating portions may also be independently controlled. More precisely, the illuminating portions may be independently switched on and off.

By taking pictures with separately illuminated portions, we can assess additional information on the acquired images such as the hair damage by comparing the two images. For example, raised hair cuticles would result in different levels of scattered light in each direction.

In particular, at least one or both illuminating portions comprise each several light sources, said light sources preferably being configured to be independently controlled. The light sources may be LEDs, more specifically High-CRI white LEDs were used to cover the whole visible spectrum as well as possible. IR LED may be used such as OSRAM broadband NIR LEDs, with or without filters to block the visible part of the spectrum of the emitted light. LEDs advantageously have a fast shutter time that will minimize potential picture-blur caused by vibrations during exposure time, especially when the inspecting device is handheld.

Having independently controlled LEDs allows for different illuminating geometries when imaging the keratinous surface, in particular hair roots near the scalp and hair lengths. When measuring hair lengths, the strands are much better behaved in their direction and can therefore be illuminated with a narrower range of light source (LEDs), lowering the specularity even more. Also there is no shadow to worry about with lengths.

In a specific embodiment, the imaging light path is substantially normal to the measurement area. After the measurement area, the light path may comprise one or several mirror diverting the light, preferably to a right angle (90°). This allows to a better and more compact design of the device. For example, the image sensor may be located in a handle and the measurement window be located in a viewing head of the device, said measurement window opening perpendicularly to a longitudinal axis of said handle.

Depending on the used image sensor and the desired light waves to be acquired, the imaging light path may be equipped with at least one wavelength filter, said filter being preferably located at the sensor.

The image sensor may be chosen in the group consisting of: a multispectral sensor, an IR sensor, a visible light imagine sensor, a RGB image sensor.

The image sensor may comprise at least one member of the group consisting of: a charge coupled device (CCD) and a complementary metal oxide semiconductor (CMOS).

In addition, the device comprises at least one electronic module configured to output the collected image data to a corresponding communication interface, preferably a wireless interface.

The invention also pertains to a system for inspecting a keratinous surface of a user, preferably a hair sample or a surface of the scalp comprising hairs, said system comprising a device according to the invention and at least one image analysis module arranged to process image data received from the device so as to output at least one real-valued characteristic property of the inspected keratinous surface. The image analysis module may be part of the device itself and output the property directly through a communication interface, preferably a wireless interface. The image analysis module may also be distinct from the device and located in a distant server or a distinct machine.

By "image analysis", it is meant the extraction of meaningful information from images; mainly from digital images by means of digital image processing techniques such as machine vision or machine learning algorithms. It does not encompass processing the image to merely display it on a monitor. Of course, the acquired image(s) may still be displayed in addition to the image analysis processing.

The invention also relates to a system for formulating a custom mixed cosmetic (namely hair, such as a hair dye formulation) treatment product in response to at least one user specific input criteria, said system comprising an inspecting system according to the invention for generating at least one of said input criteria and a plurality of cosmetically functional mixtures stored in separate containers, said mixtures being capable of combining to form a cosmetic (hair) treatment product, the system being configured to dispense two or more of the cosmetically functional mixtures each in an proportion and/or amount determined according to a recipe based on the user specific input criteria. More preferably, the product is prepared at a point of sale.

The present invention also pertains to a method for inspecting a keratinous surface of a user, preferably a hair sample or a scalp surface comprising hairs, comprising the steps of:

providing a device according to the invention so that the keratinous surface to inspect is located in the measurement area of the device, take at least one image of the keratinous surface to inspect.

More specifically, the keratinous surface is a hair strand that is placed in the measurement area. Preferably, the hair strand is arranged so that the hairs are generally orientated in a direction transverse to an axis of the illuminating portions. In another or complementary embodiment, the keratinous surface is a scalp surface comprising hairs, said hair being preferably parted along a partition line orientated in a direction transverse to an axis of the illuminating portions.

Illumination time may be between 30 and 200 ms, preferably between 50 and 200 ms.

Image(s) may be taken with both illuminating portions switched on (preferred), and/or with each illuminating portion alternatively switched on and off in sequence.

The invention also relates to a method for analyzing a keratinous surface of a user comprising the steps of inspecting said keratinous surface according to the previous method and process the at least one acquired image data in a system according to the invention so as to output at least one real-valued characteristic property of the inspected keratinous surface.

The invention also relates to a method for formulating a custom mixed cosmetic, preferably hair, treatment product, namely a hair coloration product, in response to at least one user specific input criteria, said method comprising the steps of analyzing a concerned keratinous surface of a user according to the previous method so as to obtain said user specific input criteria, and dispense two or more cosmetically functional mixtures each in an proportion and/or amount determined according to a recipe based on the user specific input criteria by using a system for formulating according to the invention.

The subject of the present application will be better understood in view of the following detailed description made in reference with the attached drawings in which:

FIG. 1 generally illustrates a system for making a personalized hair coloration cosmetic product comprising a device for inspecting an area of the scalp of a user comprising hairs and a device for dispensing cosmetically functional mixtures, namely dyes and oxidating creams, making up for the personalized product.

Figure 2:
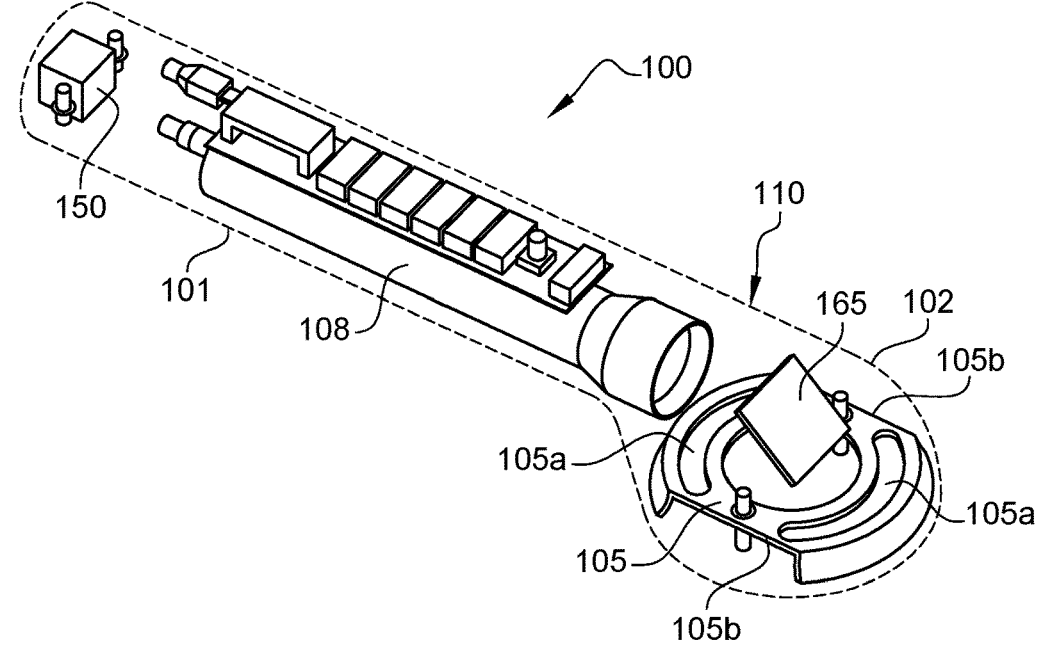

FIG. 2 is a schematic view of the device for inspecting hair sample according to the present invention as used in the system of FIG. 1.

Figure 3:
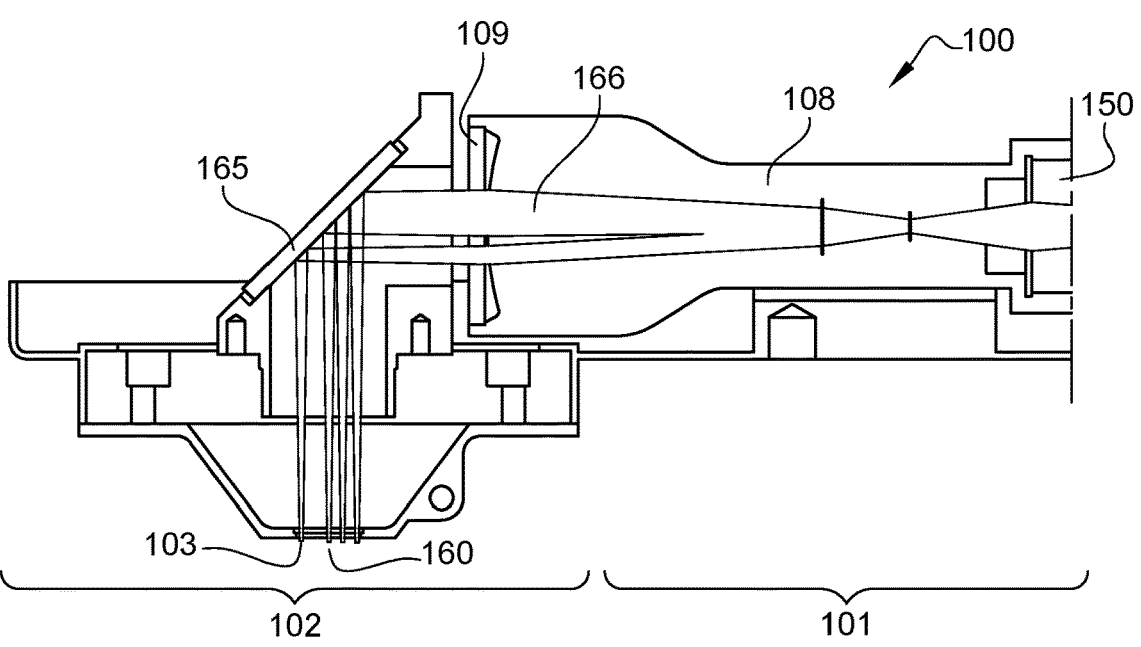
Figure 4:
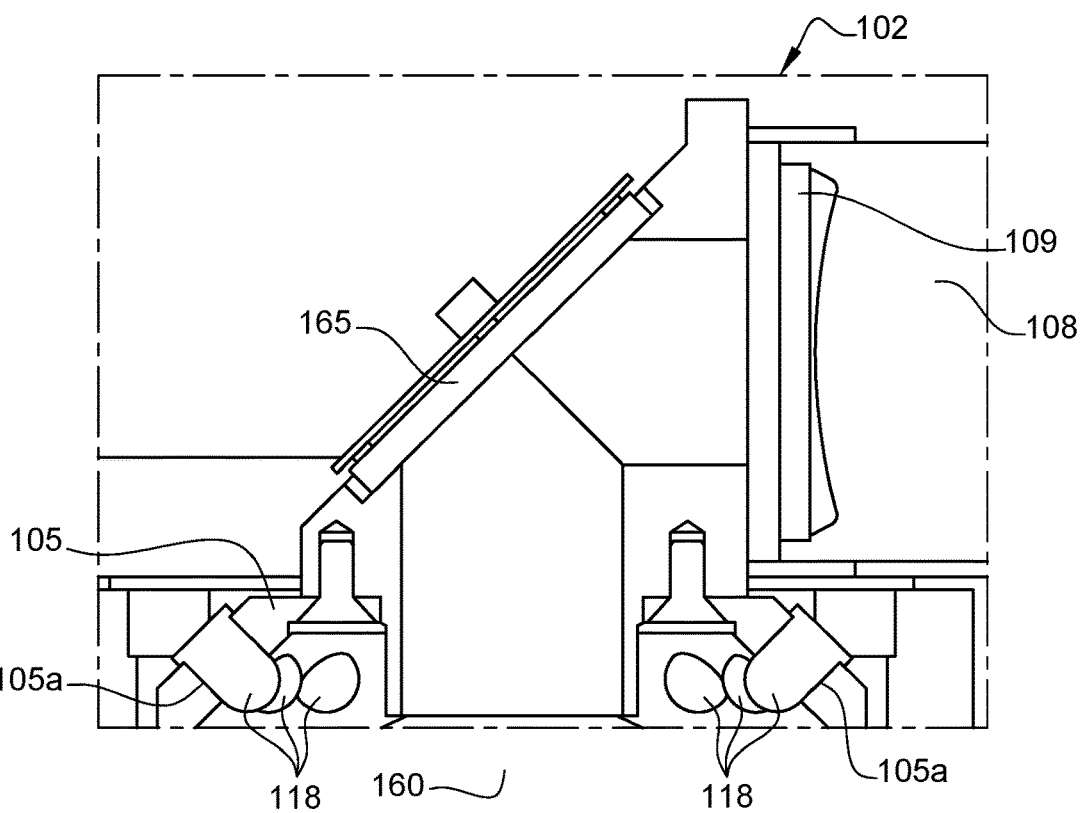
Figure 5:
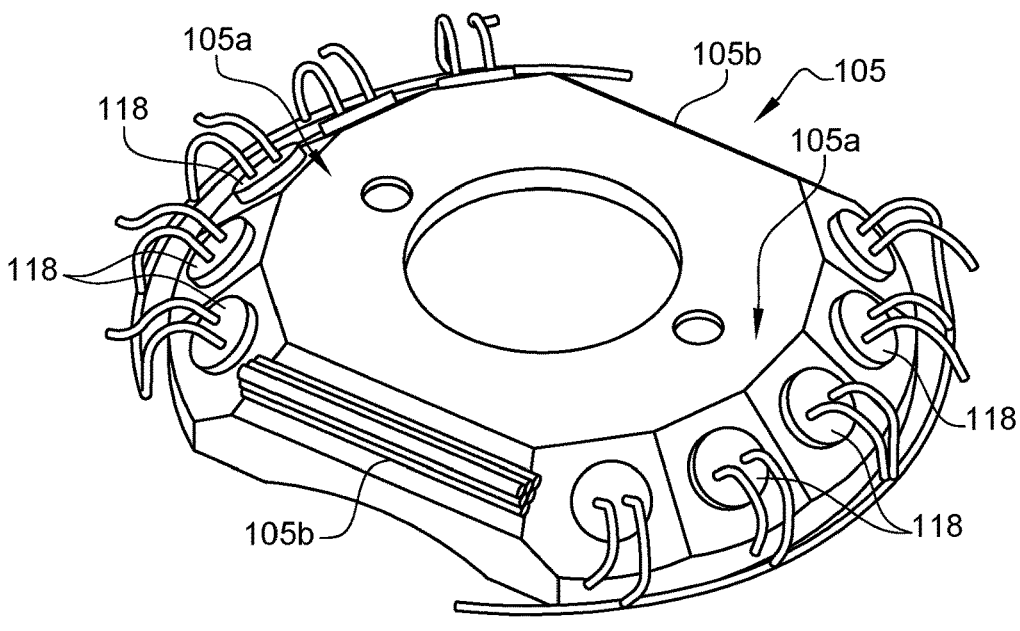
Figure 6:
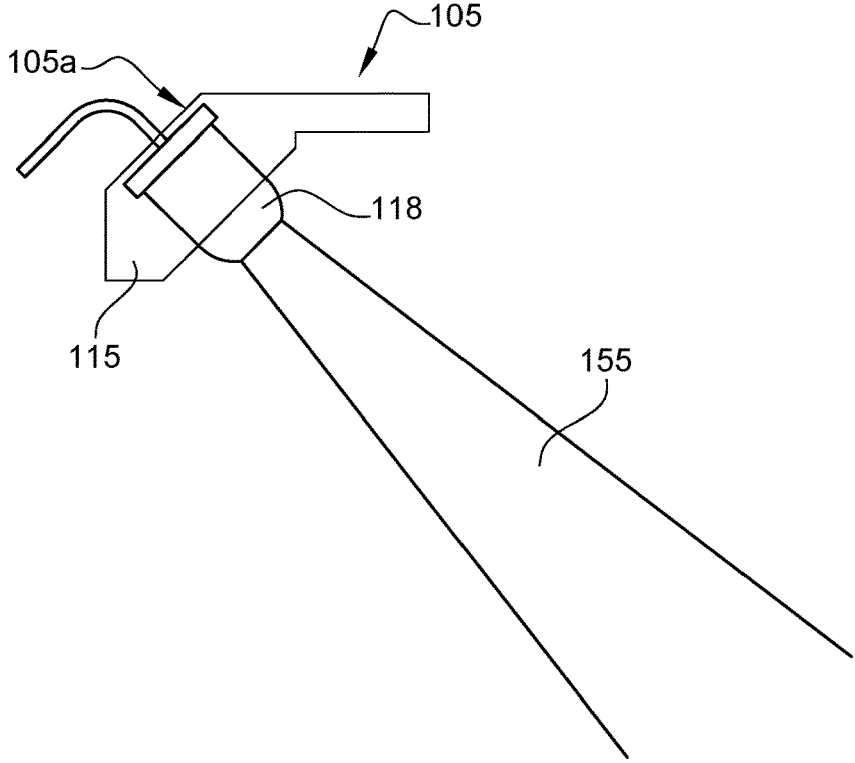

FIG. 3 is a side view of the imaging light path inside the device of FIG. 2, FIG. 4 is an internal side view of the measuring head of the device of FIG. 2, FIG. 5 is an isolated view of the illumination ring equipping the device of FIG. 2, FIG. 6 is a schematic view of the lighting arrangement and lighting orientation of the LED in the illumination ring of FIG. 5, FIG. 1 schematically shows a system 1 for formulating a custom mixed cosmetic hair coloration product in response to at least one user specific input criteria, such as hair tone h.

The system 1 comprises, on the one hand, a hair inspection device 100, also generally called hair reader, and on the other hand a dispensing device 300 carrying a plurality of cosmetically functional mixtures stored in separate containers.

More precisely, the dispensing device 300 carries a set of different hair dyes 301 and a set of oxidant base cream products 302 for mixing with the selected hair dyes in order to yielding a custom coloration product to be applied on the hairs of a customer.

The dispensing device 300 is equipped with a control board (not visible) able to selectively dispense each cosmetic product in a proportion and/or amount determined according to a recipe based on the user specific input criteria h obtained from the inspection device 100. The products are dispensed in a mixing bowl 303 where the mixture can be homogenized before application on the hair of the user.

For more details about such a system, one may refer to documents EP0443741A1 and U.S. Pat. No. 9,316,580B2 previously cited.

The inspection device 100 is part of an inspection system 200 for inspecting a hair sample 10 of a customer. Hair sample 10 is actually a surface of the scalp comprising hairs 11, but may also be a hair strand depending namely on whether we want to inspect the roots or the fiber of the hairs 11.

Inspection is performed preferably in vivo, i.e. directly on the head of the customer. To this end, the reader or inspection device 100 is associated with a processor arranged to process image data I received from the device 100 so as to output the at least one real-valued characteristic property h of the inspected keratinous surface.

The processor may be part of the inspection device 100 or be located on a distant server (not shown), acquired image data I being sent, preferably wirelessly, to the processor for image analysis.

Preparation of a custom coloration product is generally performed as follow.

First the hair reader or hair inspection device 100 is used to acquire at least an image I of the customer's hair, namely an image of a scalp portion 10 comprising hairs 11. The acquired image data I is sent to a processor to perform an image analysis algorithm and extract a relevant user specific data about the hair sample. User specific characteristic may for example be one or several parameters among hair count, hair density, hair diameter, hair color, percentage of white hairs, . . . and hair tone h.

Of course the image reader may acquire several images so that the processor may give better results. For example, the processor may use several images taken at the same location or use several images taken at different locations (hair roots and hair tips for example or forehead/backhead/tophead).

The user specific parameter or parameters h are then sent to another or same processor as input data of an algorithm configured to formulating a hair coloration composition based on said parameters and a target color according to at least one set of application rules depending on at least the user specific parameter(s).

For more details about such a system, one may refer to documents EP0443741A1 and U.S. Pat. No. 9,316,580B2 previously cited and hereby integrated by reference.

A schematic example of the hair reader or hair inspection device 100 is shown on FIG. 2. The hair reader comprises a housing 110 (dotted line) in which an image sensor 150 is arranged to receive measurement light emitted from a measuring area 160 configured to accommodate the hair sample 10, through a measurement window 103 in a front wall of the housing 110, over a corresponding imaging light path 166.

More specifically, the housing is substantially longitudinal and comprises a handle 101 (rear) and an opposite head 102 (front) accommodating said measurement window 103. The measurement window 103 is laterally arranged for ergonomic reasons and opens perpendicularly to a longitudinal axis of the handle 101. The image sensor 150 is located in the handle with most of the other electronic elements. A mirror 165 located inside the head 102 of the device 100 allows for the change of direction of the light path 166 between the measurement window 103 and the image sensor 150, so that the measurement light entering the measurement window 103 is correctly directed to the image sensor 150, roughly at 90° in the exemplified case. Of course, other orientation of the handle with regard to the measuring head are possible.

The device 100 is further equipped with an illumination ring 105 arranged in the housing 110 rear of the measurement window 103 around the imaging light path 166, said illumination ring 105 having two opposed partially peripheral illumination portions 105a separated by two opposed complementary partially peripheral non-illuminating portions 105b.

More precisely, the illumination ring 105 is made from a support plate 115 able to be secured inside the housing 110 and which presents a central orifice allowing the imaging light path 166 to go through. The support plate 115 supports a set of light sources, in the present case LEDs 118, arranged around the imaging light path 166 so as to constitute semi-peripheral illuminating portions 105b. Non illuminating portions 105b are parts of the support ring 115 deprived from light sources.

As shown, the illuminating portions 105a are arranged so that they each extends transversally to the longitudinal axis of the handle 101. As previously mentioned, when inspecting, the hairs will be preferably arranged so to have a general longitudinal axis extending along the longitudinal axis of the device, i.e. transvers to the illuminations portions 105a.

The illuminating portions 105a are further configured to illuminate the measuring area 160 through the measurement window 103 over a illumination light path 155, said illumination light path 155 having an angle of incidence of about 45° thus yielding an 45:0 illumination configuration.

In order to achieve this configuration, the light sources (LEDs 118) are mounted on the support ring 115 so as to have the desired inclination and so that their illumination cone is directed toward the measuring area with the desired angle of incidence. In an alternate embodiment, proper angle of incidence may be obtained by way of lenses directing the light emitted from the light sources in the desired direction.

As visible on FIG. 3, the measurement area 160 is substantially located at the measurement window 103. In use, the hair sample shall be preferably maintained against the measurement window 103, for example by using some clamping system or by slightly pressing the measuring head against the scalp surface of the user.

As previously mentioned, the imaging light path 166 goes through a double telecentric lens 108 before reaching the image sensor 150. As shown, the double telecentric lens is located in the handle 101 of the device between the mirror 165 and the image sensor 150. The image light path 166 also goes through a 0.5× magnification lens 109 located at the entrance of the telecentric lens 108 and part of said telecentric lens 108.

The various optical elements are chosen so that the imaging light path 166 is fixed focus and the depth of field is between 0.5 mm and 1 mm. In addition, the imaging light path has a telecentricity below 1 degree.

The device 100 also carries a control board for piloting all or some of the various elements and namely manage the illumination ring while taking pictures.

The device 100, and more particularly its control board, is configured so that the illuminating portions 105a may be independently controlled, thus allowing to take pictures with both illuminating portions 105a light up or only one of them. In the latter case, the device 100 will advantageously take at least two pictures, one for each illuminating portion subsequently on.

Advantageously, the light sources LEDs 118 forming the illuminating portions may be independently controlled Device according to any one of claims 1 to 9, characterized in that at least one or both illuminating portions comprise each several light sources, said light sources preferably being configured to be independently controlled.

The electronic control boar of the device 100 also includes an electronic module configured to output the collected image data to a corresponding communication interface with the image analysis module (external).

The invention claimed is:

1. A device for inspecting a scalp surface of a user, the device comprising a housing in which an image sensor is arranged to receive measurement light emitted from a measuring area configured to accommodate a keratinous surface of the scalp surface, the image sensor configured to acquire an image of the scalp surface that includes the keratinous surface through a measurement window in a front wall of the housing, over a corresponding imaging light path, the device being further equipped with an illumination ring arranged in the housing rear of the measurement window around the imaging light path, said illumination ring having two opposed partially peripheral illumination portions extending over a sector of 30 to 60° and separated by two opposed complementary partially peripheral non-illuminating portions, the illumination portions being further configured to illuminate the measuring area by directing light emitted from the illumination portions from rear of the measurement window through the measurement window to the measuring area over an illumination light path, said illumination light path having an angle of incidence of 45° so as to form a 45:0 measurement configuration, wherein the device is configured so that both illumination portions may be on when the image is taken.

2. The device according to claim 1, wherein the measurement area is substantially located at the measurement window.

3. The device according to claim 1, wherein the imaging light path is equipped with a double telecentric lens.

4. The device according to claim 1, wherein the imaging light path is equipped with a 0.5× magnification lens.

5. The device according to claim 1, wherein the imaging light path is fixed focus.

6. The device according to claim 1, wherein a depth of field is between 0.5 mm and 1 mm.

7. The device according to claim 1, wherein the imaging light path has a telecentricity below 1 degree.

8. The device according to claim 1, wherein the illumination portions of the light ring extend over a sector of 45°.

9. The device according to claim 1, wherein it is configured so that the illumination portions can also be independently controlled.

10. The device according to claim 1, wherein at least one or both illumination portions each comprise several light sources, said light sources being configured to be independently controlled.

11. The device according to claim 1, wherein the imaging light path is substantially normal to the measurement area.

12. The device according to claim 1, wherein the imaging light path is equipped with at least one wavelength filter, said filter being located at the sensor.

13. The device according to claim 1, wherein it comprises at least one electronic module configured to output the collected image data to a corresponding communication interface.

14. The device according to claim 1, wherein the image sensor is chosen in the group consisting of: a multispectral sensor, an IR sensor, a visible light image sensor, a RGB image sensor.

15. The device according to claim 1, wherein the image sensor comprises at least one member of the group consisting of: a charge coupled device (CCD) and a complementary metal oxide semiconductor (CMOS).

16. A system for inspecting a scalp surface of a user or a hair sample, said system comprising a device according to claim 1 and at least one processor arranged to process image data received from the device so as to output at least one real-valued characteristic property of the inspected keratinous surface.

17. The system for formulating a custom mixed cosmetic treatment product in response to at least one user specific input criteria, said system comprising an inspecting system according to claim 16 and separate containers configured to store a plurality of cosmetically functional mixtures, said mixtures being capable of combining to form a cosmetic treatment product, the system being configured to dispense two or more of the cosmetically functional mixtures each in a proportion and/or amount determined according to a recipe based on the user specific input criteria.

18. A method for inspecting a scalp surface of a user or a hair sample, comprising the steps of: providing a device according to claim 1 so that the keratinous surface to inspect is located in the measurement area of the device, taking at least one image of the keratinous surface to inspect with both illumination portions being switched on.

19. The method for analyzing a scalp surface of a user or a hair sample, comprising the steps of inspecting said hair sample by a method according to claim 18 and processing the acquired image data in a system for inspecting a scalp surface of a user or a hair sample, the system further comprising at least one processor arranged to process image data received from the device so as to output at least one real-valued characteristic property of the inspected keratinous surface.

20. The method for formulating a custom mixed cosmetic treatment hair product, namely a hair coloration product, in response to at least one user specific input criteria, said method comprising the steps of analyzing a concerned keratinous surface of a user according to claim 19 so as to obtain said user specific input criteria, and dispensing two or more cosmetically functional mixtures each in a proportion and/or amount determined according to a recipe based on the user specific input criteria by using a system for formulating a custom mixed cosmetic treatment product in response to at least one user specific input criteria, said system comprising a device for inspecting the scalp surface of a user or a hair sample, comprising a housing in which an image sensor is arranged to receive measurement light emitted from a measuring area configured to accommodate the keratinous surface, through a measurement window in a front wall of the housing, over a corresponding imaging light path, the device further including an illumination ring arranged in the housing rear of the measurement window around the imaging light path, said illumination ring having two opposed partially peripheral illumination portions extending over a sector of 30 to 60° and separated by two opposed complementary partially peripheral non-illuminating portions, the illuminating portions being further configured to illuminate the measuring area through the measurement window over an illumination light path, said illumination light path having an angle of incidence between 30 to 60°, preferably 45° so as to form a 45:0 measurement configuration, wherein the device is configured so that both illumination portions may be on when an image is taken, wherein the system further includes separate containers configured to store a plurality of cosmetically functional mixtures, said mixtures being capable of combining to form a cosmetic treatment product, the system being configured to dispense two or more of the cosmetically functional mixtures each in a proportion and/or amount determined according to a recipe based on the user specific input criteria.

\* \* \* \* \*